(12) United States Patent
Howe

(10) Patent No.: US 11,890,313 B2
(45) Date of Patent: *Feb. 6, 2024

(54) NATURAL DRUGS FOR THE TREATMENT OF INFLAMMATION AND MELANOMA

(71) Applicant: HERBALIFE INTERNATIONAL, INC, Los Angeles, CA (US)

(72) Inventor: Bruce L. Howe, San Diego, CA (US)

(73) Assignee: HERBALIFE INTERNATIONAL, INC., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,434

(22) Filed: Sep. 2, 2022

(65) Prior Publication Data

US 2022/0409691 A1 Dec. 29, 2022

Related U.S. Application Data

(60) Division of application No. 16/983,715, filed on Aug. 3, 2020, now Pat. No. 11,607,439, which is a continuation of application No. 15/829,716, filed on Dec. 1, 2017, now Pat. No. 10,772,926.

(60) Provisional application No. 62/435,608, filed on Dec. 16, 2016.

(51) Int. Cl.
| | |
|---|---|
| *A61K 36/9068* | (2006.01) |
| *A61K 36/9066* | (2006.01) |
| *A61K 36/324* | (2006.01) |
| *A61K 9/127* | (2006.01) |
| *A61K 31/685* | (2006.01) |
| *A61K 31/56* | (2006.01) |
| *A61K 31/12* | (2006.01) |
| *A61K 9/14* | (2006.01) |

(52) U.S. Cl.
CPC .......... *A61K 36/9068* (2013.01); *A61K 9/127* (2013.01); *A61K 9/14* (2013.01); *A61K 31/12* (2013.01); *A61K 31/56* (2013.01); *A61K 31/685* (2013.01); *A61K 36/324* (2013.01); *A61K 36/9066* (2013.01)

(58) Field of Classification Search
None
See application file for complete search history.

(56) References Cited

U.S. PATENT DOCUMENTS

| | | |
|---|---|---|
| 3,932,657 A | 1/1976 | Rahman |
| 4,235,871 A | 11/1980 | Papahadjopoulos et al. |
| 4,311,712 A | 1/1982 | Evan et al. |
| 5,013,556 A | 5/1991 | Woodle et al. |

FOREIGN PATENT DOCUMENTS

JP 2004196696 A * 7/2004

OTHER PUBLICATIONS

Remington's Pharmaceutical Sciences, Eighteenth Edition Edited by Alfonso R. Gennaro, Grafton D. Chase, Ara Der Marderosian et al. Published by Mack Publishing Company, Easton, PA 18042, 1990 (TOC).
Eichberg, J., in Kirk-Othmer Encyclopedia of Chemical Technology, edited by M. Grayson, 3rd edn., vol. 14, John Wiley & Sons, New York, 1981, pp. 250-269.
Peterson and Johnson, editors, Encyclopedia of Food Science, Avi Publishing Co. 1978, pp. 461,467.
Szhuhaj ed., 1989, Lecithins: Sources, Manufacture & Uses, The American Oil Chemists' Society (TOC).
Prosise, W.E., Commercial Lecithin Products: Food Use of Soybean Lecithin, Chapter 8 in Szhuhaj et al., Lecithins, The American Oil Chemists' Society.
Justo et al.; Evaluation of in vitro anti-inflammatory effects of crude ginger and rosemary extracts obtained through supercritical CO2 extraction on macrophage and tumor cell line: the influence of vehicle type: BMC Complement Altern Med. Oct. 29, 2015; 15:390.
Mostafa et al. Boswellia carteri liquisolid systems with promoted anti-inflammatory activity: Curr Drug Deliv. 2015; 12(4):454-63.
Multisupreme Vitamins; http://www.nutrisupremevitamins.com/bosellia-curcumin-and-ginger-root/.
Wendel, 2014, Lecithin, in Kirk-Othmer ed. Encyclopedia of Chemical Technology, 14:1-19.
Wolf et al., 1978, Lecithin, in Peterson et al., eds. Encyclopedia of Food Science, The Avi Publishing Company, Inc., Westport, Connecticut, pp. 461-467.

* cited by examiner

*Primary Examiner* — Michael V Meller
(74) *Attorney, Agent, or Firm* — Knobbe Martens Olson & Bear LLP

(57) ABSTRACT

The invention is directed to natural drug compositions comprising turmeric, *boswellia* and ginger. Methods for the use of the inventive drug compositions in the treatment of inflammatory disorders and melanoma are within the scope of the invention.

12 Claims, 2 Drawing Sheets

NATURAL DRUGS FOR THE TREATMENT OF INFLAMMATION AND MELANOMA

CROSS-REFERENCE TO RELATED APPLICATIONS

This application is a divisional of U.S. application Ser. No. 16/983,715 filed Aug. 3, 2020, which is a continuation of U.S. application Ser. No. 15/829,716 filed Dec. 1, 2017, which claims priority under 35 U.S.C. § 119(e) to Provisional Application No. 62/435,608, filed Dec. 16, 2016. The entire contents of these applications are incorporated herein by reference for all purposes.

BACKGROUND OF THE INVENTION

Field of the Invention

The invention is in the field of drug compositions derived from natural sources.

Description of the Related Art

Inflammation can be considered a central feature of many pathophysiological conditions that are initiated in response to tissue and cellular damage by pathogens, noxious stimuli, such as chemicals and physical injury. Such damage leads to the secretion of cytokines and other mediators as well as activation and migration of immune cells. These mediators add to the generation of excess free radicals such as reactive oxygen species (ROS) and reactive nitrogen species (RNS) which lead to DNA damage. Acute inflammation is a short-term response that usually results in healing as leukocytes infiltrate the damaged region, removing the stimulus and repairing the tissue. Chronic inflammation, by contrast, is a prolonged, dysregulated and maladaptive response that involves active inflammation and tissue destruction. Such persistent inflammation is associated with many chronic human conditions and diseases, including allergy, atherosclerosis, cancer, arthritis and autoimmune diseases. Inflammation is currently treated by NSAIDs (non-steroidal anti-inflammatory drugs). Unfortunately, these drugs lead to blood clots and consequently increase the risk for heart attacks and strokes. Natural products are rich source for discovery of new drugs because of their chemical diversity. Natural products from medicinal plants may play a major role in treating many diseases associated with inflammation.

SUMMARY OF THE INVENTION

The invention provides natural drug compositions developed from turmeric, *boswellia* and ginger. The invention further provides methods for using such drug compositions in the treatment of inflammatory disorders and melanoma.

DEFINITIONS

Figure 1:
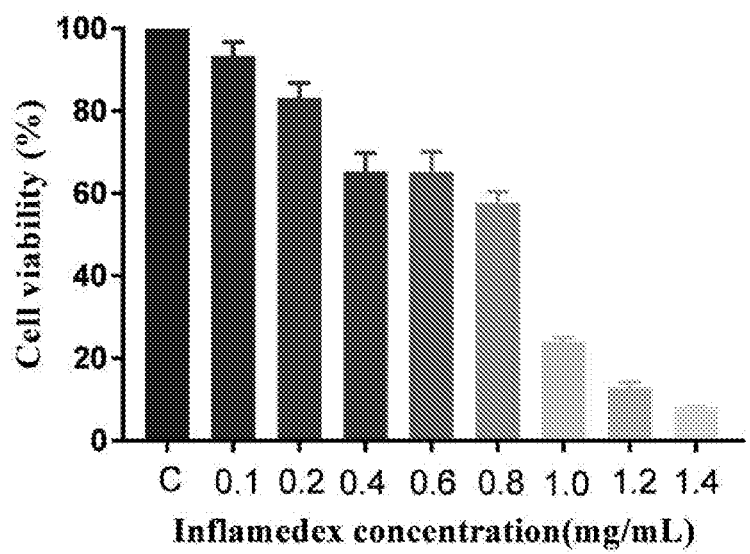
FIG. 1 shows the cytotoxic effect of an embodiment of the drug composition on RAW 264.7 cells using an MTT assay.

As used herein, the term "active agent" refers to the components of the inventive drug composition which have a desired biological or pharmacological effect in a subject. The term "active agent" includes turmeric, *boswellia*, ginger, or combination thereof.

As used herein, the term "about" or "approximately" refers to a quantity, level, value, number, frequency, percentage, dimension, size, amount, weight or length that is the same as the stated value, or that varies by as much as 30, 25, 20, 25, 10, 9, 8, 7, 6, 5, 4, 3, 2 or 1% to the referenced quantity, level, value, number, frequency, percentage, dimension, size, amount, weight or length. In particular embodiments, the terms "about" or "approximately" when preceding a numerical value indicates the stated value plus or minus a range of 15%, 10%, 5%, or 1%, or any intervening range thereof.

As used herein, the term "bioavailability" refers to the degree and rate at which a substance is absorbed into a living system or is made available at the site of physiological activity.

As used herein, the term "bioenhancer" refers to a substance that increases the bioavailability of a material that has a biological or pharmacological effect in a subject compared to the bioavailability of the material in the absence of the substance.

As used herein, the term "*boswellia*" refers to any material obtained from a genus of trees and shrubs in the order Sapindales, known for their fragrant resin. *Boswellia* includes materials obtained from *B. sacra* (synonyms *B. carteri* and *B. bhaw-dajiana*), *B. frereana*, *B. papyrifera*, and *B. serrata*, *B. ameero*, *B. bullata*, *B. dalzielii*, *B. dioscorides*, *B. elongata*, *B. nana*, *B. neglecta*, *B. ogadensis*, *B. pirottae*, *B. popoviana*, *B. rivae*, *B. socotrana*, and mixtures thereof. Such materials can be obtained from the leaves, flowers, stems, roots, resin, and/or bark of such trees and shrubs. *Boswellia* includes an extract, fresh and/or dried material obtained from the leaves, flowers, stems, roots, resin, and/or bark of such trees and shrubs. *Boswellia* includes acids derived from the resin of such trees and shrubs.

As used herein, the term "effective concentration" or "effective amount" is used to describe an amount or concentration of an active agent or drug composition according to the present invention which is used to produce an intended result. In the case of the present invention, effective concentrations are generally concentrations which are effective to treat an inflammatory disorder or melanoma.

As used herein, the term "ginger" refers to any material obtained from the flowering plant *Zingiber ojicinale*. Ginger for use with the invention includes, but is not limited to, raw ginger, ginger oil, ginger extract, gingerols, or a combination thereof. Ginger includes, but is not limited to, ginger, ginger oil, ginger extract, gingerols, or a combination thereof, derived from the root of the ginger plant.

As used herein, the term "lecithin," refers to any or all of the phosphatides, pure or in blends comprising phosphatidylcholine, phosphatidylethanolamine, phosphatidylinositol, and/or phosphatidylserine, and/or other phosphatides regarded as lecithins.

As used herein, the terms "treating" or "treatment" or "to treat" or "alleviating" or "to alleviate" refer to both 1) therapeutic measures that cure, slow down, lessen symptoms of, and/or halt progression of a pathologic condition or disorder and 2) prophylactic or preventative measures that prevent and/or slow the development of a targeted pathologic condition or disorder. Thus, those in need of treatment include those having the disorder; those prone to have the disorder; and those in whom the disorder is to be prevented.

As used herein, the term "turmeric" refers to any material obtained from the herb *Curcuma longa*. Turmeric for use with the invention includes, but is not limited to, raw turmeric, turmeric oil, turmeric extract, or a combination thereof.

DETAILED DESCRIPTION

The invention generally relates to drug compositions developed from natural sources. More particularly, the invention relates to drug compositions developed from synergistic combinations of turmeric, *boswellia* and ginger. Methods of using the drug compositions for the treatment of inflammatory disorders and melanoma are also within the scope of this invention.

In one aspect, the invention provides a drug composition comprising at least one of turmeric, *boswellia* and ginger. One or more of the turmeric, *boswellia* and ginger can be in the form of fresh or dried material. Dried material can be in the form of a powder, for example. The drug compositions can comprise extracts of at least one of turmeric, *boswellia* and ginger. The drug composition can comprise: turmeric extract and *boswellia* extract; turmeric extract and ginger extract; *boswellia* extract and ginger extract; or turmeric extract, *boswellia* extract, and ginger extract.

The relative amounts of each extract may vary depending on the disorder that is targeted for use of the drug composition. The drug composition can comprise, for example, about 50% turmeric, about 30% *boswellia*, and about 20% ginger. It is further contemplated that these percentages, may vary (+/−) up to 80%. Thus, the drug composition can comprise about 95% to about 30% turmeric, about 54% to about 6% *boswellia*, and about 36% to about 20% ginger. It is further understood that the percentages disclosed in this paragraph may vary, or be offset, by an amount corresponding to the amount of any bioenhancer that is added to increase the bioavailability of the turmeric, *boswellia*, and/or ginger (i.e. active agents).

The drug compositions of the invention can comprise one or more of turmeric extract, *boswellia* extract, and ginger extract. Turmeric extract may be standardized to contain about 95-98% curcuminoids. Turmeric extracts for use with the invention may be standardized to contain curcuminoids in an amount of about 100%, 99% 98%, 97%, 96%, 95%, 94%, 93%, 92%, 91%, 90%, 80%, 70%, 60%, 50%, 40%, 30%, 20%, 10%, or any amount intervening these amounts. Ginger extract may contain gingerols, including 8-gingerol, 10-gingerol, and 12-gingerol. Ginger extracts for use with the invention may be standardized to contain one or more of these gingerols in an amount of about 100%, 99% 98%, 97%, 96%, 95%, 94%, 93%, 92%, 91%, 90%, 80%, 70%, 60%, 50%, 40%, 30%, 20%, 10%, 5%, 2%, or any amount intervening these amounts. In a non-limiting embodiment, the ginger extract is standardized to about 5% of one or more gingerols. In another non-limiting embodiment, the ginger extract is standardized to about 20% of one or more gingerols.

*Boswellia* for use with the drug composition can comprise *boswellia* extract. The *boswellia* extract can be standardized for boswellic acid. *Boswellia* extracts can be standardized to contain one or more boswellic acids in amount of about 100%, 99% 98%, 97%, 96%, 95%, 94%, 93%, 92%, 91%, 90%, 80%, 70%, 60%, 50%, 40%, 30%, 20%, 10%, 5%, or any amount intervening these amounts. In one non-limiting embodiment, the *boswellia* extract is standardized to about 30% boswellic acid. The boswellic acid to which the boswellic extract is standardized can be acetyl-11-keto-beta-boswellic acid (AKBA).

*Boswellia* for use with the invention can be *boswellia* gum resin. The gum resin of *boswellia* is a complex mixture comprising: *boswellia* oil fraction (BOIL) containing essential oil/*boswellia* volatile oil fraction (BVOIL); non-acidic *boswellia* low polar gum resin extract fraction (BLPRE); boswellic acids (BA); and sugars and polysaccharide fraction (BSUG). The *boswellia* gum resin can be standardized to contain one or more of BOIL, BVOIL, BLPRE, BA and BSUG in an amount of about 100%, 99% 98%, 97%, 96%, 95%, 94%, 93%, 92%, 91%, 90%, 80%, 70%, 60%, 50%, 40%, 30%, 20%, 10%, or any amount intervening these amounts. It is contemplated that the drug composition can be formulated with *boswellia* in the form of BIOL, BVOIL, BLPRE, BA, BSUG, or a combination thereof. It is contemplated that the drug composition can be formulated with *boswellia* in the form of purified BIOL, purified BVOIL, purified BLPRE, purified BA, purified BSUG, or a combination thereof.

In a specific, non-limiting example, the drug composition of the invention comprises about 50% turmeric extract standardized to about 95% curcuminoids, about 30% *boswellia* extract standardized to about 30% AKBA, and about 20% ginger extract standardized to about 20% gingerols. In another embodiment, the drug composition comprises: 100 mg to 10,000 mg of turmeric standardized to about 25% to about 99% curcuminoids; 100 mg to 10,000 mg *boswellia* standardized to about 5% to about 99% AKBA; and 100 mg to 10,000 mg of ginger standardized to about 5% to about 99% gingerols. In another embodiment, the drug composition can comprise 250 mg turmeric extract standardized to about 95% curcuminoids, 150 mg. *boswellia* standardized to about 30% AKBA, and 100 mg ginger standardized to about 20% gingerols.

In some aspects, the drug compositions are formulated for administration to a subject, such as a human subject. Such formulations may assume any form suitable for oral administration to a subject including, but not limited to pills, capsules, tablets, liquids (e.g. beverages, or drops), gummies, pastes, emulsions, drops, syrups, gels, softgels, powders, or food supplements. The invention also contemplates formulating the drug compositions as cosmeceuticals, including, but not limited to, creams, gels, powders, milks, emulsions, liquids, sprays, foams, sticks and pastes. The drug compositions can be formulated for administration by any suitable means, including topically, orally, sublingually, buccally, intra-ocularly, intravenously, intramuscularly, intra-arterially, by suppository, intranasally, subcutaneously, parenterally, intravaginally, rectally, or by inhalation. Thus, the drug compositions may be formulated with a suitable pharmaceutical carrier (e.g. artificial pharmaceutical carriers) for administering according to any of the preceding routes of administration. The drug compositions can comprise one or more carriers including, but not limited to, sodium citrate, dicalcium phosphate, fillers or extenders (such as starches, lactose, sucrose, glucose, mannitol, and silicic acid), binders (such as, for example, carboxymethylcellulose, alginates, gelatin, polyvinylpyrrolidinone, sucrose, and acacia), disintegrating agents (such as agar-agar, calcium carbonate, potato or tapioca starch, alginic acid, silicates, and sodium carbonate), buffering agents and combinations thereof.

The drug compositions can be in a dosage form that includes but is not limited to powders, pills, tablets, pellets, capsules, thin films, solutions, sprays, syrups, linctuses, lozenges, pastilles, chewing gums, pastes, vapours, suspensions, solutions, emulsions, ointments, creams, lotions, liniments, gels, drops, topical patches, buccal patches, beads, gummies, gels, sols, injections and the like. The drug composition can comprise at least one pharmaceutically acceptable excipient. Suitable excipients for use with the drug compositions include, but are not limited to, those disclosed in Remington's Pharmaceutical Sciences, 18$^{th}$ ed. the disclosure of which is incorporated herein by reference in its entirety for all purposes. The pharmaceutically acceptable excipient can be an artificial pharmaceutical carrier.

In some aspects of the invention, the drug composition is formulated to achieve increased bioavailability of one or more of the active agents in the drug composition. As used herein, the phrase "increasing bioavailability" refers to increasing the bioavailability of one or more active agents in the drug composition relative to a control set of conditions. The term "active agent" as used herein includes turmeric, *boswellia* and ginger. Active agents in the drug composition further include the constituent compounds included in the turmeric, *boswellia* and/or ginger. Constituent compounds in turmeric include, but are not limited to, curcuminoids. As used herein, the term "curcuminoids" refers to curcumin, demethoxycurcumin, and bisdemethoxycurcumin. Constituent compounds in ginger include, but are not limited to gingerols, including 8-gingerol, 10-gingerol, and 12-gingerol. Constituent compounds in *boswellia* include, but are not limited to, BIOL, BVOIL, BLPRE, BA, BSUG, AKBA, or a combination thereof.

The drug composition can be formulated with a bioenhancer to achieve increased bioavailability of the active agents. Accordingly, the drug composition can comprise at least one of turmeric, *boswellia*, ginger, and an amount of bioenhancer effective to increase the bioavailability of at least one of the turmeric, *boswellia* and ginger. The drug composition can comprise turmeric extract, *boswellia* extract, ginger extract, and an amount of bioenhancer sufficient to increase the bioavailability of at least one of the turmeric extract, *boswellia* extract, and ginger extract. In some aspects, the bioenhancer is purified. As used herein, the term "purified" refers to a compound having been separated from a component of the composition in which it was originally present. The bioenhancer can be present in the drug composition in an amount of about 10%, 9%, 8%, 7%, 6%, 5%, 4%, 3%, 2%, 1%, 0.5%, or 0.25%, with the remaining portion of the composition being turmeric, *boswellia* and ginger. The bioenhancer can be present in the drug composition in an amount of about 10%, 9%, 8%, 7%, 6%, 5%, 4%, 3%, 2%, 1%, 0.5%, or 0.25%, with the remaining portion of the composition being turmeric extract, *boswellia* extract and ginger extract. The drug composition can comprise 1% bioenhancer, with the remaining portion of the composition comprising turmeric, *boswellia* and ginger. In a non-limiting embodiment, the drug composition comprises 1% bioenhancer, with the remaining portion of the composition comprising turmeric extract, *boswellia* extract and ginger extract. It will be understood that the amount of the one or more of the active agents (e.g. turmeric, *boswellia* and ginger) as disclosed herein will be reduced by the corresponding amount of amount of bioenhancer that is used for increasing the bioavailability of the active agents. For example, a drug composition comprising 50% turmeric, 30% *boswellia*, and 20% ginger may comprise 49% turmeric, 30% *boswellia*, 20% ginger, and 1% bioenhancer.

Bioenhancers for use with the invention include, but are not limited to, lecithin, turmeric oil, *boswellia* oil, ginger oil (e.g. ginger root oil), or a combination thereof. The turmeric oil, *boswellia* oil and ginger oil can be volatile oils, non-volatile oils, or a combination thereof.

Lecithins for use with the drug compositions can be edible lecithins. Edible lecithins are well-known, widely available, and are described and defined in detail in the public literature. For example, they are described in: Kirk Othmer, Encyclopedia of Chemical Technology, Volume 14, pp. 250-269; in the Encyclopedia of Food Science, Peterson and Johnson, editors, Avi Publishing Co. 1978, pp. 461,467; and LECITHINS, edited by Bernard F. Szuhaj, and Gary R. List, which was published by the American Oil Chemists' Society as a monograph. (Also see especially Chapter 8, Commercial Lecithin Products; Food Use of Soybean Lecithin, by W. E. Prosise). The descriptions of all these references are incorporated by reference herein in their entirety and for all purposes. Lecithin for use with the drug compositions may be sunflower lecithin.

In a non-limiting embodiment wherein the drug composition is formulated with bioenhancers, the drug composition can comprise (i) a turmeric component comprising about 98% turmeric extract (standardized to about 95% curcuminoids), about 1% lecithin, and about 1% turmeric oil, (ii) a *boswellia* component comprising about 98% *boswellia* extract (standardized to about 30% of one or more boswelic acids), about 1% *boswellia* oil, and about 1% lecithin, and (iii) a ginger component comprising about 98% ginger extract (standardized to about 20% gingerols), about 1% ginger oil, and about 1% lecithin. In such embodiments, the drug composition can comprise about 50% of the turmeric component, about 30% of the *boswellia* component, and about 20% of the ginger component. It will be understood that in embodiments where one or more of the extracts contains oil of the extracted base material, the amount of oil used as a bioenhancer will be in addition to the oil contained in the extract. For example, wherein the drug composition comprises *boswellia* extract containing *boswellia* oil, the drug composition can contain 1% *boswellia* oil in addition to the *boswellia* oil contained in the extract. It will be understood that the lecithin, boswellic acid(s), *boswellia* oil, and ginger oil of the drug composition can comprise one or more of these materials as disclosed herein. For example, the lecithin can be sunflower lecithin, the boswellic acid component can comprise AKBA, the *boswellia* oil can comprise *boswellia serrata* oil, and the ginger oil can comprise ginger root oil.

In some aspects, the invention provides methods for treating inflammation. In some aspects, the invention provides methods for treating an inflammatory disorder. The methods can be practice by administering to a subject an effective amount of the drug composition to a subject in need of treatment for inflammation or an inflammatory disorder. As used herein, the term "subject" refers to a mammal, including but not limited to humans, non-human primates, cattle, sheep, dogs, cats, rats, mice, horses, goats, pigs or poultry (e.g. chickens, ducks, and geese). The inflammatory disorder can be an inflammatory disorder that is mediated by macrophage activity, wherein administration of the drug composition inhibits macrophage pro-inflammatory activity. The inflammatory disorder can be sepsis-related multiple organ dysfunction/multiple organ failure, microbial infection, acute brain/lung/hepatic/renal injuries, neurodegenerative disorders, tumorigenesis, osteoporosis/osteonecrosis, cardiovascular disease (e.g. atherosclerosis), metabolic diseases, Type II diabetes, localized inflammation, and autoimmune diseases. The inflammatory disorder can be a gastrointestinal disorder. The gastrointestinal disorder can be gastroparesis, post-operative ileus or inflammatory bowel disease. The autoimmune disease can be rheumatoid arthritis.

In some aspects, the invention provides a method for treating melanoma in a subject in need thereof comprising administering to the subject a drug composition as disclosed herein. The term "melanoma" includes primary melanoma and metastatic melanoma. In certain embodiments, a subject is successfully "treated" for melanoma according to the methods of the present invention if the patient shows one or more of the following: a reduction in the number of, or complete absence of, cancer or tumor cells; a reduction in the tumor size; inhibition of, or an absence of, cancer or tumor cell infiltration into peripheral organs including, for example, the spread of tumor into soft tissue and bone; inhibition of, or an absence of, tumor metastasis; inhibition of, or an absence of, tumor growth; relief of one or more symptoms associated with melanoma; reduced morbidity and mortality; improvement in quality of life; reduction in tumorigenicity, tumorigenic frequency, or tumorigenic capacity of a tumor; reduction in the number or frequency of cancer stem cells in a tumor; reduction in the number or frequency of tumor initiating cells in a tumor; differentiation of tumorigenic cells to a non-tumorigenic state; or some combination of effects.

In methods the of treatment disclosed herein, the drug composition can be administered to the subject topically, orally, sublingually, buccally, intra-ocularly, intravenously, intramuscularly, intra-arterially, by suppository, intranasally, subcutaneously, parenterally, intravaginally, rectally, by inhalation, or a combination thereof. In a preferred embodiment, the drug composition is administered orally.

In some aspects of the invention, one or more of the active agents or bioenhancers of the drug composition are organic. As used herein, the term "organic" refers to, relating to, yielding, or involving the use of food produced with the use of feed or fertilizer of plant or animal origin without employment of chemically formulated fertilizers, growth stimulants, antibiotics, or pesticides. In some aspects, organic components for use with the drug composition are certified by an organization that is approved and recognized by the USDA National Organics Program.

The drug compositions can comprise one or more agents for improving the palatability of the composition. For example, the drug compositions can comprise sweeteners, aromatic compounds, flavourings, or a combination thereof. Similarly, the drug compositions can comprise agents to increase the antioxidant and/or nutritional value of the compositions. Such agents include, but are not limited to, vitamins, minerals, proteins, amino acids, and carbohydrates.

In some aspects of the invention, the drug composition can be encapsulated. Such encapsulation may be accomplished via liposomes, nanospheres and/or micelles. Various methods of preparing the encapsulation of the drug compositions are described, for example, in U.S. Pat. Nos. 3,932,657, 4,235,871, 4,311,712, and 5,013,556, the disclosures of which are incorporated herein by reference for all purposes. In one non-limiting embodiment, the liposome comprises a lecithin liposome.

The present disclosure is further described in the light of the following non-limiting examples which are set forth for illustration purpose only and not to be construed for limiting the scope of the disclosure.

EXAMPLE 1—DRUG FORMULATION

Turmeric extract was standardized to 95% curcuminoids, boswellia extract was standardized to 30% AKBA, and ginger extract was standardized to 20% gingerols. These components were combined to achieve a composition comprising 50% of the turmeric extract, 30% of the boswellia extract, and 20% of the ginger extract. The mixture was dried to a powder. This drug composition was used in the following example.

EXAMPLE 2—DRUG EFFECTS ON INFLAMMATION AND MELANOMA CELL VIABILITY

Cell Culture

The murine macrophage RAW 264.7 and B16-F10 melanoma cell line was purchased from the National Centre for Cell Science (Pune, India). RAW 264.7 cells were cultured in Dulbecco's modified Eagle's medium (DMEM; GIBCO Inc., NY, USA) supplemented with 100 U/ml of penicillin, 100 lg/ml of streptomycin and 10% fetal bovine serum (FBS; GIBCO Inc., NY, USA). The cells were incubated in an atmosphere of 5% CO2 at 37° C. and were sub-cultured every 3 days.

MTT Assay for Assessment of Cytotoxicity

The effect of the drug composition on RAW 264.7 and B16-F10 melanoma cell line was observed by MTT (3-(4, 5-dimethylthiazol-2-yl)-2,5-diphenyl tetrazolium bromide) assay. Cells were counted on haemocytometer and 5000 cells/well were plated in 96 well plate in 100 µl of complete media (containing 10% of FBS). Cells were treated with different concentrations (0.1 0.2 0.4 0.6 0.8 1.0 and 1.2 mg/mL) of the drug composition for 48 hr. After the stipulated time, MTT solution (5 mg/ml) was added to each well and incubated for 3 hr. The purple precipitate of formazan was dissolved in 150 µl of DMSO (Sigma-Aldrich) by proper mixing. The colour absorbance of each well was recorded at 570 nm in Multiscan EX reader with a reference serving as blank. Then, $IC_{50}$ value of the drug composition was calculated.

Morphological Study Under Phase Contrast Microscopy

B16-F10 melanoma cells were treated with different concentrations (0.4 and 0.8 mg/mL) of the drug composition for 48 hr. Following incubation, the cells were observed under phase contrast microscope at 20× magnification.

Determination of NO Production

After pre-incubation of RAW 264.7 cells ($1.5 \times 10^5$ cells/ml) with LPS (1 µg/ml) plus samples at 37° C. for 24 h, the quantity of nitrite accumulated in the culture medium was measured as an indicator of NO production (Lee et al., 2007). Briefly, a 100 µl of cell culture medium was mixed with 100 µl of Griess reagent (1% sulphanilamide and 0.1% naphthylethylenediamine dihydrochloride in 2.5% phosphoric acid), the mixture was incubated at room temperature for 10 min, and the absorbance at 540 nm was measured in a microplate reader (Mutiscan EX). Fresh culture medium was used as a blank in every experiment.

Figure 2:
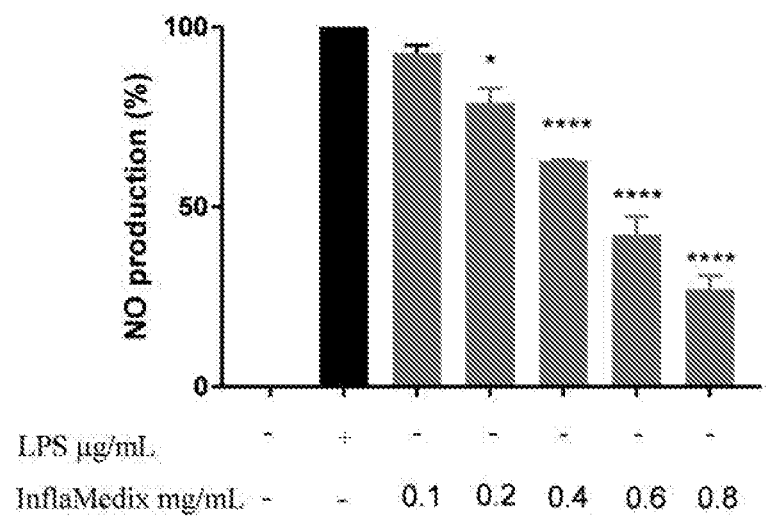
FIG. 2 shows the inhibitory effect of an embodiment of the drug composition on NO production in LPS-stimulated RAW 264.7 cells. The production of NO was assayed in the culture medium of cells stimulated with LPS (1 µg/ml) for 24 h in the presence of the drug composition at different concentrations.

Results
Cytotoxicity and Inhibitory Effect of NO Production of the Drug Composition The cytotoxic effect of the drug composition was assessed by MTT assay. The drug composition did not influence the cytotoxicity, with only the highest concentration (1.2 mg/mL) affecting cell viability at around 24.3% of RAW 264.7 cells (FIG. 1). In order to study the potential anti-inflammatory effect of the drug composition, RAW 264.7 cells were treated with 1 μg/ml LPS with or without different concentration of the drug composition. After 24 h, nitrite concentrations were determined as an indicator of NO production. As shown in FIG. 2, the drug composition significantly inhibited the LPS-induced production of NO.

Reduction in Viability of B16-F10 Melanoma Cells

Figure 3:
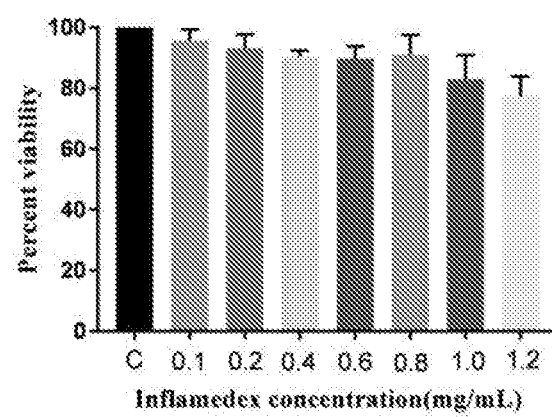
FIG. 3 shows the cytotoxic effect of an embodiment of the drug composition on melanoma cells using an MTT assay.

MTT assay was performed to evaluate the cytotoxic effect of the drug composition on B16-F10 melanoma cells were treated with different concentrations (0.1, 0.2, 0.4, 0.6, 0.8, 1.0 and 1.2 mg/mL) for 48 hr. A significant reduction of cell viability was seen in dose dependent manner when compared with the control or vehicle treated B16-F10 melanoma cells. The calculated $IC_{50}$ value for 48 hr is 0.85 mg/mL (FIG. 3).

Figure 4:
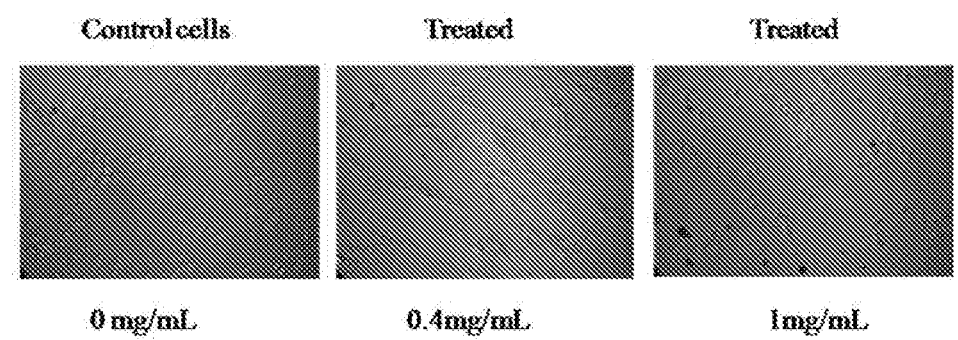
FIG. 4 Shows the morphological changes observed in B16-F10 melanoma cells treated with an embodiment of the drug composition. Cells were treated with 0.4 and 1 mg/mL of the drug composition for 48 hr.

Phase Contrast Microscopic Observations of B16-F10 Melanoma Cells after Treatment Morphological alterations were observed in treated B16-F10 cells in comparison to the control or vehicle treated cells. In case of control cells, the shape of B16-F10 cell is polygonal but after treatment with different concentrations of the drug, the shape became spherical and cell numbers decreased (FIG. 4).

Statistical Analysis

All the measurements were made in triplicate and all values were represented as means±standard error. Statistical analysis was performed by one-way ANOVA followed by Student 't' test using GraphPad software prism 7.01.

DISCUSSION AND CONCLUSION

Lee et al., 2011; Poltorak et al., 1998 and Kanno et al., 2006. Reported that macrophages play critical roles in immune reaction, allergy, and inflammation. These cells induce inflammatory reaction, and initiate and maintain specific immune responses by releasing different types of cytokines. Macrophage activation by lipopolysaccharides (LPS), which are derived from gram-negative bacteria cell walls, results in the release of several inflammatory mediators including nitric oxide (NO), cyclooxygenase (COX)-2, interleukin (IL)-6, IL-1b, and tumor necrosis factor (TNF)-a. Over-expression of the inflammatory mediators in macrophage is involved in many inflammation related diseases, such as atherosclerosis, rheumatoid arthritis, autoimmune diseases. Thus, inhibition of inflammatory mediators produced by macrophages is crucial for managing inflammatory diseases.

In conclusion, from our preliminary data we found that the drug composition showed significant inhibition of NO in LPS stimulated RAW 264.7 cells. In addition, it also showed anticancer effect on B16-F10 melanoma cells.

What is claimed is:

1. A method for treating inflammation in a human, the inflammation due to a disorder selected from the group consisting of Type II diabetes, inflammatory bowel disease, and rheumatoid arthritis, the method comprising:
    identifying a human having inflammation due to a disorder in the human, wherein the disorder is selected from the group consisting of Type II diabetes, inflammatory bowel disease, and rheumatoid arthritis; and
    administering to the human a composition comprising about 50% turmeric extract, about 30% Boswellia extract, and about 20% ginger extract.
2. The method of claim 1, wherein the turmeric extract is standardized to about 95% curcuminoids.
3. The method of claim 2, wherein the turmeric extract comprises about 1% lecithin and about 1% turmeric oil.
4. The method of claim 1, wherein the boswellia extract is standardized to about 30% boswellic acid.
5. The method of claim 4, wherein the boswellic acid comprises acetyl-11-keto-beta-boswellic acid.
6. The method of claim 4, wherein the boswellia extract comprises about 1% lecithin and about 1% boswellia oil.
7. The method of claim 1, wherein the ginger extract is standardized to about 20% gingerols.
8. The method of claim 7, wherein the ginger extract comprises about 1% lecithin and about 1% ginger oil.
9. The method of claim 8, wherein the composition is encapsulated within a liposome.
10. The method of claim 1, wherein the disorder is Type II diabetes.
11. The method of claim 1, wherein the disorder is inflammatory bowel disease.
12. The method of claim 1, wherein the disorder is rheumatoid arthritis.

* * * * *